US012496436B2

(12) United States Patent
Huang

(10) Patent No.: US 12,496,436 B2
(45) Date of Patent: Dec. 16, 2025

(54) HOLLOW BALLOON CATHETER DEVICE FOR GUIDING BLOOD FLOW

(71) Applicant: Shih-Chieh Huang, Taichung (TW)

(72) Inventor: Shih-Chieh Huang, Taichung (TW)

(73) Assignee: NO.1 BIOTECHNOLOGY CO., LTD.

( * ) Notice: Subject to any disclaimer, the term of this patent is extended or adjusted under 35 U.S.C. 154(b) by 57 days.

(21) Appl. No.: 18/666,790

(22) Filed: May 16, 2024

(65) Prior Publication Data

US 2025/0352775 A1 Nov. 20, 2025

(51) Int. Cl.
*A61M 25/10* (2013.01)

(52) U.S. Cl.
CPC ...... *A61M 25/1018* (2013.01); *A61M 25/104* (2013.01)

(58) Field of Classification Search
CPC ............ A61M 25/1018; A61M 25/104; A61M 2025/1043; A61M 2025/1047; A61M 2025/105; A61M 2025/1052; A61M 2025/1072; A61M 2025/1095; A61M 2025/1097
See application file for complete search history.

(56) References Cited

U.S. PATENT DOCUMENTS 5,257,974 A * 11/1993 Cox .................... A61M 25/104 604/103.05
2003/0004462 A1* 1/2003 Halpin ............... A61B 17/0057 604/99.04
2009/0270964 A1* 10/2009 Huetter ................... A61F 2/958 604/103
2019/0388656 A1* 12/2019 Shameli ............ A61M 25/1002

* cited by examiner

*Primary Examiner* — Tan-Uyen T Ho
*Assistant Examiner* — Bridget E. Rabaglia

(57) ABSTRACT

A hollow balloon catheter device (100) includes a catheter portion (10) including a passage (101) defined therethrough, and a balloon (20) located at one end of the catheter portion (10). An inflation tube (30) passes through the passage (101) and extends into a balloon element (202). A blood flow channel (201) extends through the balloon (20). The balloon (20) is inflated via the inflation tube (30) to dilate a blocked blood vessel (200), while the blood flow channel (201) forms an open configuration and communicates with the blood vessel (200) after the balloon (20) is inflated so that blood continues to flow through the blood flow channel (201). This ensures that blood flow is not hindered or blocked, eliminating concerns about blood reflux or blockage for the doctor and avoiding operational errors due to time constraints.

3 Claims, 7 Drawing Sheets

HOLLOW BALLOON CATHETER DEVICE FOR GUIDING BLOOD FLOW

BACKGROUND OF THE INVENTION

1. Fields of the Invention

The present invention relates to a hollow balloon catheter device capable of guiding blood flow, specifically designed for use in the medical field.

2. Descriptions of Related Art

The use of balloon catheters carries risks, as in some patients, blood vessels may rebound after dilation, causing re-narrowing. Sometimes, multiple dilations are necessary, and eventually, doctors may recommend the placement of high-tech metal stents to reduce recurrence. However, during each use of the balloon catheter, especially in the treatment of internal cardiac vessels, the balloon, once inflated, fills and expands, blocking blood flow due to its placement. Consequently, the time for using balloon catheters to expand cardiac blood vessels is limited, resulting in a brief period of myocardial hypoxia of approximately 30 seconds. Beyond 30 seconds, it can lead to unstable vital signs, and even trigger arrhythmias, ultimately increasing the risk of surgery.

Furthermore, as shown in FIG. 11, the wire structure 400 of the balloon catheter 300 is equipped with small holes 500 to allow blood flow. However, the diameter of these holes 500 varies depending on the organ location. For instance, in surgeries involving the heart, the diameter of the holes 500 in the wire structure 400 is only 0.014 cm. Such a small diameter makes it difficult for blood to flow through the vessels, and the surface tension at the opening of these small holes 500 can further hinder blood flow, leading to blockages.

The present invention intends to provide a hollow balloon catheter device capable of guiding blood flow to eliminate the shortcomings mentioned above.

SUMMARY OF THE INVENTION

The present invention relates to a hollow balloon catheter device positioned at a blocked blood vessel, and comprises a catheter portion and a balloon. The catheter portion internally includes a passage defined therethrough, and the balloon is located at one end of the catheter portion. An inflation tube passes through the passage and extends into at least one balloon element. At least one blood flow channel extends through the balloon. The balloon is inflated via the inflation tube to dilate the blocked blood vessel. The at least one blood flow channel forms an open configuration and communicates with the blood vessel after the balloon is inflated, allowing the catheter device to dilate the blood vessel while blood continues to flow through the at least one blood flow channel.

The primary object of the present invention is to provide doctors with more time to perform surgical procedures involving balloon catheter dilation, allowing them to focus on the specific vascular sites without concerns about blood blockage or reflux affecting other organs (such as myocardial tissue), especially the heart. This improvement enhances safety for patients by reducing the likelihood of complications. It addresses the shortcomings of conventional balloon catheter usage in surgery, which often leads to vascular blockage, reflux, and impacts on peripheral organ function, requiring high-risk procedures to ensure surgical success.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 1:
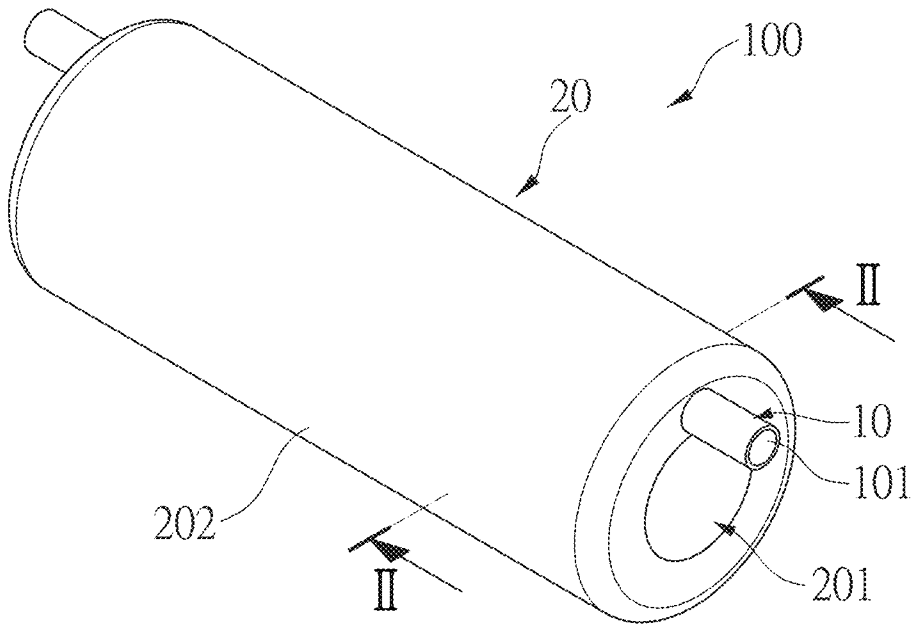
FIG. 1 is a perspective view of the first embodiment of the present invention.
Figure 2:
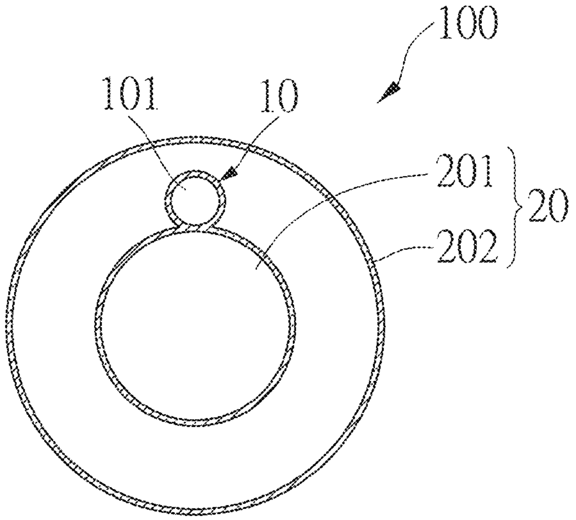
FIG. 2 is a cross sectional view, taken along line II-II of FIG. 1.

Referring to FIGS. 1 to 10, the present invention provides a hollow balloon catheter device 100 capable of guiding blood flow, primarily positioned at a blocked blood vessel 200, and used to dilate the blocked blood vessel 200 to allow smooth blood flow.

The catheter device 100 comprises a catheter portion 10 and a balloon 20, wherein the catheter portion 10 internally forms a passage 101, and the balloon 20 is located at one end of the catheter portion 10. The balloon 20 includes at least one blood flow channel 201 and at least one balloon element 202 located inside the balloon 20. An inflation tube 30 passes through the passage 101 and extends into the at least one balloon element 202. The insertion of the inflation tube 30 tightly adheres to the junction between the passage 101 and the at least one balloon element 202, ensuring a sealed state inside the at least one balloon element 202 to prevent air leakage during inflation. The at least one blood flow channel 201 extends from one end to the other end of the balloon 20. The inflation of the at least one balloon element 202 via the inflation tube 30 causes it to expand, thereby dilating the blocked blood vessel 200. Upon inflation of the at least one balloon element 202, the at least one blood flow channel 201 forms an open configuration and communicates with the blood vessel 200, allowing the catheter device 100 to dilate the blood vessel 200 while blood continues to flow through the at least one blood flow channel 201.

Figure 3:
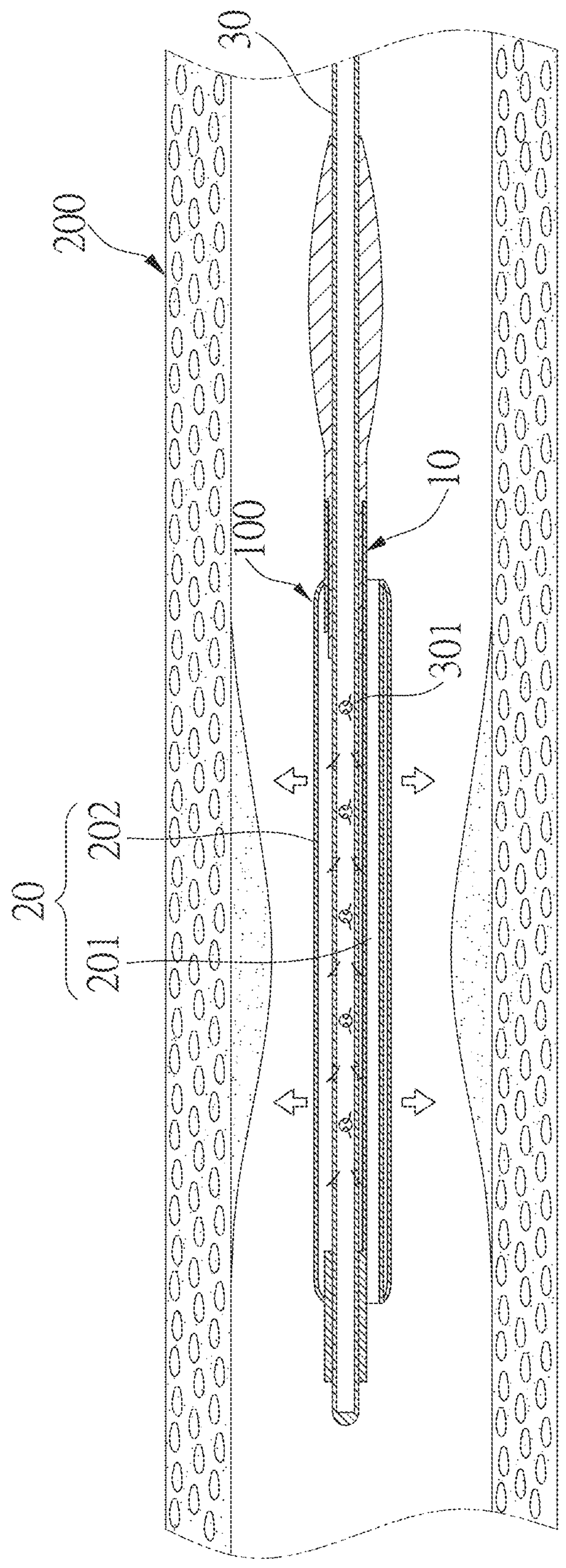
FIG. 3 is a cross sectional view to illustrate the usage state of the present invention when applied inside a blood vessel and not yet inflated.
Figure 4:
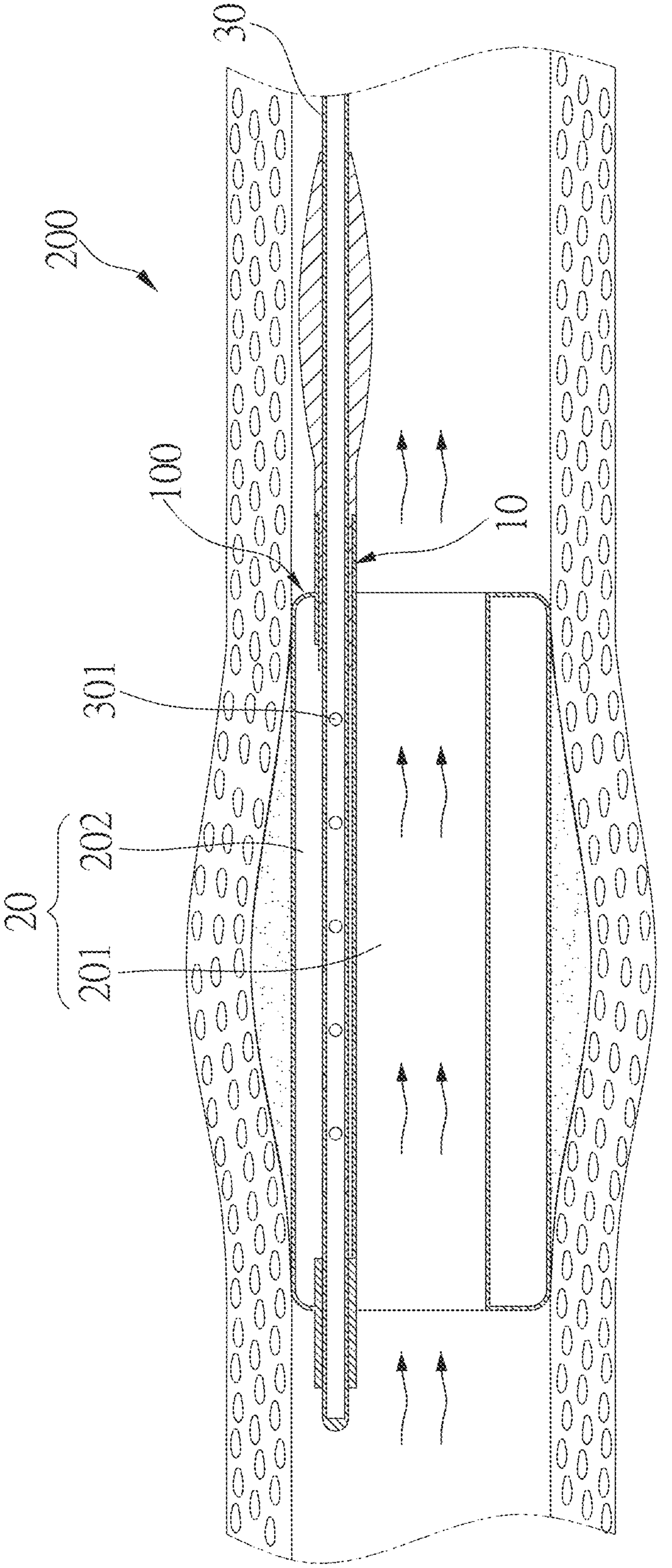
FIG. 4 is a cross sectional view to illustrate the usage state of the present invention when applied inside a blood vessel and inflated.

When a doctor determines that a patient needs vascular dilation, the catheter device 100 is inserted into the blood vessel 200 and gradually moved until the balloon 20 is positioned at the desired site for dilation. Subsequently, the inflation tube 30 is inserted from one end of the catheter portion 10 into the passage 101 and advanced into the balloon 20, where it is stopped. Then, external inflation equipment is used to supply gas, which enters through the inflation tube 30 and gradually inflates the at least one balloon element 202 of the balloon 20. As the at least one balloon element 202 gradually expands, it dilates the portion of the blood vessel 200 that requires treatment. The inflation of the at least one balloon element 202 also causes the at least one blood flow channel 201 to gradually open up. "Opening up" refers to gradually revealing its channel state. Once the at least one blood flow channel 201 is fully expanded, it becomes contiguous with the interior of the blood vessel 200, allowing blood to flow smoothly during treatment. This structure is particularly important for organs, especially the heart, as it does not cause temporary obstruction of blood flow. Maintaining stable blood flow ensures that all organs receive normal blood supply. Unlike conventional balloon catheters that directly occlude the entire blood vessel upon inflation, preventing blood circulation and potentially causing severe organ damage, pain, ischemia, discomfort, infarction, arrhythmias, and clot formation. The use of this invention not only allows for vascular dilation therapy but also maintains blood flow within the blood vessel 200, ensuring treatment safety, as shown in FIGS. 3 and 4.

The present invention has multiple embodiments. Please refer to FIGS. 3 and 4. To enable the inflation tube 30 to supply and release gas and thereby inflate and deflate the at least one balloon element 202, the inflation tube 30 is further equipped with at least one port 301 at one end inside the at least one balloon element 202. Gas is guided by the inflation tube 30 and discharged through the at least one port 301 to fill the at least one balloon element 202. After inflation, the at least one balloon element 202 expands to dilate the blood vessel 200, and gas is drawn from the at least one balloon element 202 through the at least one port 301. Once the at least one balloon element 202 is deflated, the catheter device 100 can be removed from the blood vessel 200.

In the first embodiment of the present invention, as illustrated in FIGS. 1 to 4, the cross-section of the at least one blood flow channel 201 is circular, while the cross-section of the at least one balloon element 202 of the balloon 20 is annular or ring-shaped. The at least one balloon element 202 is hollow, with the blood flow channel 201 providing a pathway for blood flow. The at least one outer inflatable balloons 202 expands upon inflation, dilating the blood vessel 200 and facilitating smooth blood flow. Please refer to FIGS. 1 to 4.

Figure 5:
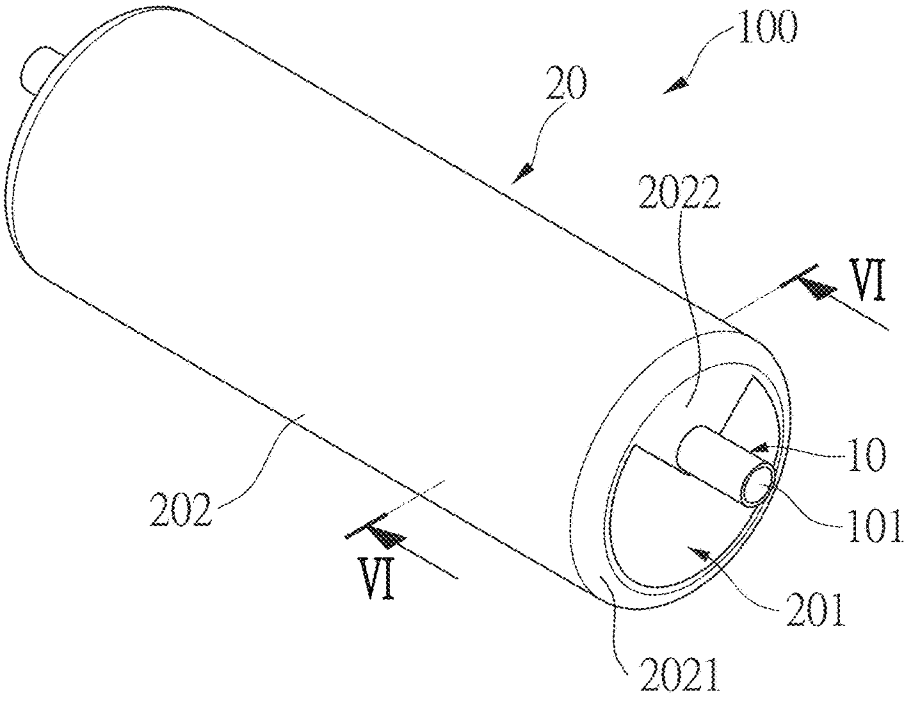
FIG. 5 is a perspective view of the second embodiment of the present invention.
Figure 6:
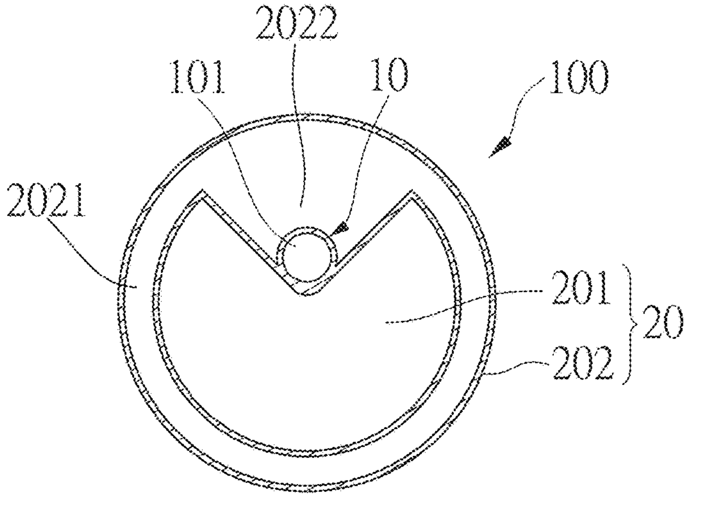
FIG. 6 is a cross sectional view, taken along line VI-VI of FIG. 5.

In the second embodiment of the present invention, as shown in FIGS. 5 and 6, the cross-section of the at least one blood flow channel 201 is fan-shaped, while the at least one balloon element 202 further includes an outer filling region 2021 and an inner filling region 2022 which is in communication with the outer filling region 2021. The at least one blood flow channel 201 and the inner filling region 2022 together form a circular-shaped area, with the at least one blood flow channel 201 occupying three-quarters of the circular-shaped area, and the inner filling region 2022 occupying one-quarter of the circular-shaped area. Blood flows through the fan-shaped blood flow channel 201 (the aforementioned proportions are not limiting to the shape; various ratios can also be used, primarily describing the configuration of this embodiment).

Figure 7:
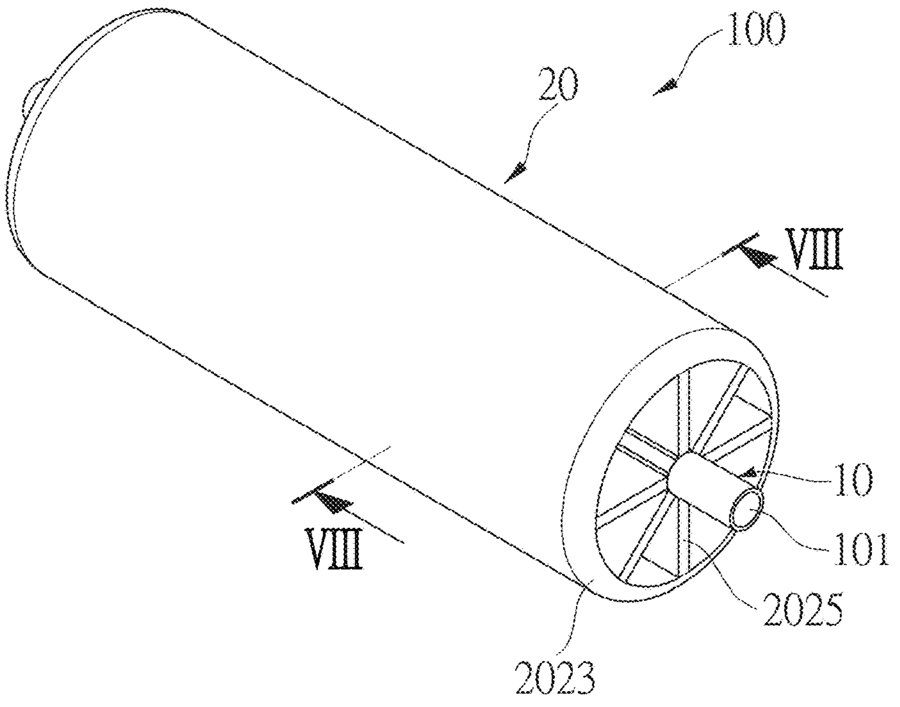
FIG. 7 is a perspective view of the third embodiment of the present invention.
Figure 8:
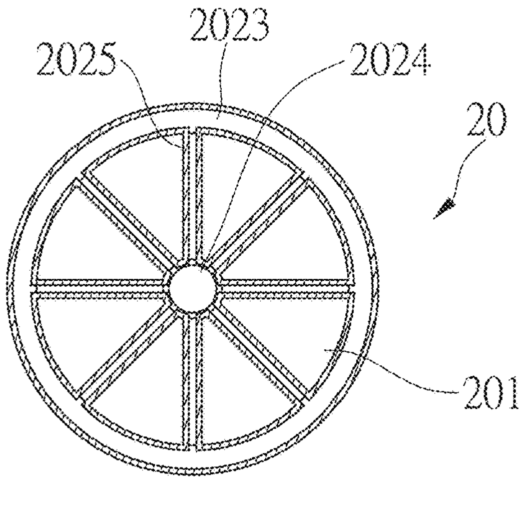
FIG. 8 is a cross sectional view, taken along line VIII-VIII of FIG. 7.

In the third embodiment of the present invention, as shown in FIGS. 7 and 8, the at least one balloon element 202 of the balloon 20 comprises an outer filling region 2023, a central filling region 2024, and multiple filling connecting ribs 2025. The outer filling region 2023 is annular, and the central filling region 2024 is located inside the outer filling region 2023, forming a hollow tubular structure. Each filling connecting rib 2025 is connected at one end to the outer peripheral side of the central filling region 2024 and radiates to connect to the inner wall surface of the outer filling region 2023. The filling connecting ribs 2025 are also hollow and communicate with both the outer filling region 2023 and the central filling region 2024. The inflation tube 30 extends into the central filling region 2024 to supply and release gas, and the gas fills the central filling region 2024, the filling connecting ribs 2025, and the outer filling region 2023. Additionally, the arrangement of the filling connecting ribs 2025 separates the outer filling region 2023 and the central filling region 2024 to form multiple blood flow channels 201 (illustrated with eight blood flow channels 201) in the intermediate space 2029. Each blood flow channel 201 communicates individually with the blood vessel 200, allowing blood to flow through multiple pathways.

Figure 9:
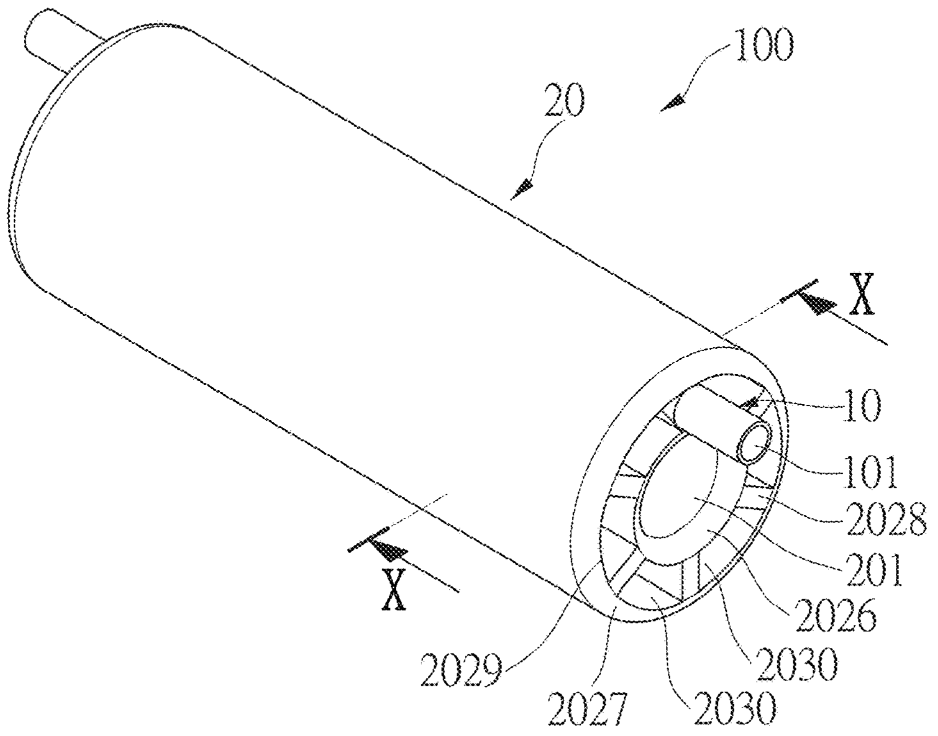
FIG. 9 is a perspective view of the fourth embodiment of the present invention.
Figure 10:
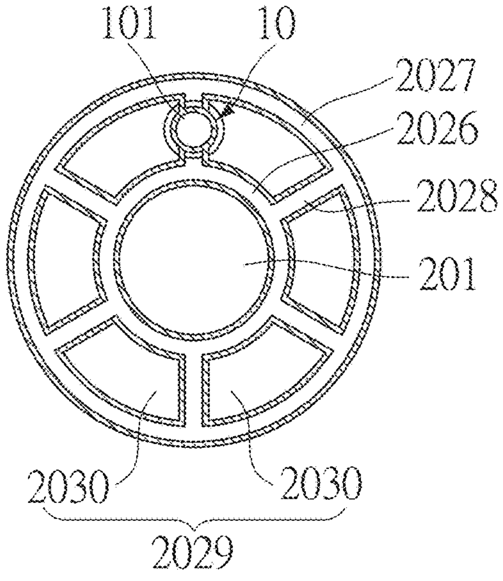
FIG. 10 is a cross sectional view, taken along line X-X of FIG. 9.
Figure 11:
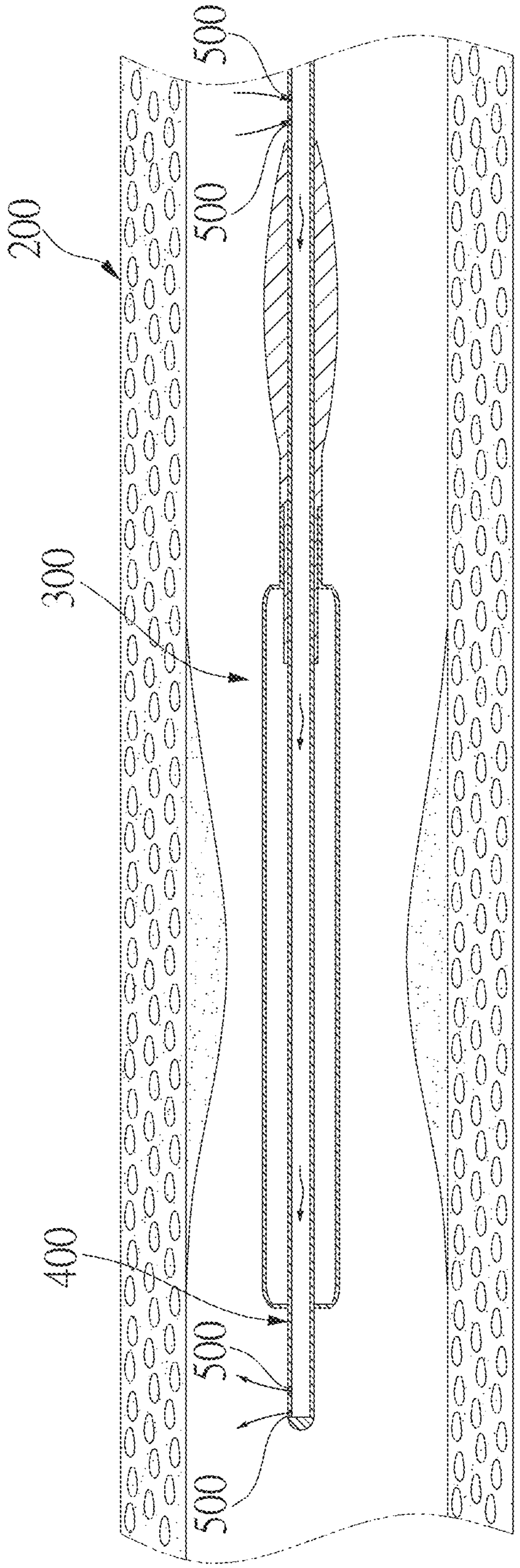
FIG. 11 is a cross sectional view of a conventional balloon catheter.

In the fourth embodiment of the present invention, as shown in FIGS. 9 and 10, the at least one balloon element 202 of the balloon 20 includes an inner filling region 2026, an outer filling region 2027 and multiple filling guiding ribs 2028. The inner filling region 2026 and the outer filling region 2027 together form a tubular structure with hollow annular cross-sections. The inner filling region 2026 is located inside the outer filling region 2027 to form concentric circles. The inner filling region 2026 and the outer filling region 2027 are separated by an intermediate space 2029. The multiple filling guiding ribs 2028 are located in the intermediate space 2029 and are each connected at one end to the inner filling region 2026. The filling guiding ribs 2028 radiate towards the outer filling region 2027 and are connected to the inner wall surface of the outer filling region 2027. Each filling guiding rib 2028 is hollow and communicates with both the inner filling region 2026 and the outer filling region 2027. When the inflation tube 30 supplies gas, the gas fills the inner filling region 2026, the outer filling region 2027 and the filling guiding ribs 2028. The filling guiding ribs 2028 separate the intermediate space 2029 to form multiple side flow channels 2030 (illustrated with six side flow channels 2030). Additionally, the at least one blood flow channel 201 passes through the inner filling region 2026, and both the blood flow channel 201 and the side flow channels 2030 communicate with the blood vessel 200, allowing blood within the blood vessel 200 to be maintained through the blood flow channel 201 and the side flow channels 2030.

While we have shown and described the embodiment in accordance with the present invention, it should be clear to those skilled in the art that further embodiments may be made without departing from the scope of the present invention.

What is claimed is:

1. A hollow balloon catheter device (100) positioned at a blocked blood vessel (200), comprising:

a catheter portion (10) and a balloon (20), the catheter portion (10) internally including a passage (101) defined therethrough, and the balloon (20) located at one end of the catheter portion (10);

an inflation tube (30) passing through the passage (101) and extending into at least one balloon element (202);

at least one blood flow channel (201) extending through the balloon (20), and; wherein the balloon (20) comprises an inner filling region (2026), an outer filling region (2027), and multiple filling guiding ribs (2028), the inner filling region (2026) is located within the outer filling region (2027), a space (2029) is formed between the inner filling region (2026) and the outer filling region (2027), the multiple filling guiding ribs (2028) are located within the space (2029) and each are connected between the inner filling region (2026) and an inner wall surface of the outer filling region (2027), each filling guiding rib (2028) communicates with the inner filling region (2026) and the outer filling region (2027), each filling guiding rib (2028) separates the space (2029) to form multiple side flow channels (2030), the at least one blood flow channel (201) extends through the inner filling region (2026), and the at least one blood flow channel (201) and each side flow channel (2030) are in communication with the blood vessel (200), allowing blood within the blood vessel (200) to be maintained through the blood flow channel (201) and the side flow channels (2030).

2. The hollow balloon catheter device as claimed in claim 1, wherein the balloon (20) internally comprises the at least one balloon element (202), the inflation tube (30) has at least one port (301) located at one end inside the at least one balloon element (202) which guides gas through the inflation tube (30) to be discharged from the at least one port (301) to fill the at least one balloon element (202), the at least one balloon element (202) expands and dilates the blood vessel (200), the at least one port (301) withdraws gas from inside the at least one balloon element (202) to deflate the at least one balloon element (202), so that the catheter device (100) is removed from the blood vessel (200).

3. The hollow balloon catheter device as claimed in claim 1, wherein a cross-section of the at least one blood flow channel (201) is circular, a cross-section of the balloon (20) is ring-shaped.

* * * * *